United States Patent
Myhre

(10) Patent No.: US 7,334,413 B2
(45) Date of Patent: Feb. 26, 2008

(54) APPARATUS, SYSTEM AND METHOD FOR OBSERVING COMBUSTION CONDITIONS IN A GAS TURBINE ENGINE

(75) Inventor: Douglas C. Myhre, Eden Prairie, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 96 days.

(21) Appl. No.: 10/841,765

(22) Filed: May 7, 2004

(65) Prior Publication Data

US 2005/0247066 A1 Nov. 10, 2005

(51) Int. Cl.
*F02C 7/00* (2006.01)
(52) U.S. Cl. .............................. 60/803; 431/13; 431/14
(58) Field of Classification Search ............... 60/39.24, 60/39.27, 39.281, 803; 431/13, 14
See application file for complete search history.

(56) References Cited

U.S. PATENT DOCUMENTS

| | | | |
|---|---|---|---|
| 2,975,785 A | | 3/1961 | Sheldon |
| 3,689,773 A | | 9/1972 | Wheeler |
| 4,521,088 A | | 6/1985 | Masom |
| 4,709,155 A | | 11/1987 | Yamaguchi et al. |
| 5,071,105 A | * | 12/1991 | Donze et al. .................. 266/51 |
| 5,257,496 A | * | 11/1993 | Brown et al. ............ 60/39.281 |
| 5,608,515 A | | 3/1997 | Shu et al. |
| 5,828,797 A | | 10/1998 | Minott et al. |
| 6,640,548 B2 | * | 11/2003 | Brushwood et al. .......... 60/776 |
| 6,688,534 B2 | | 2/2004 | Bretz |
| 2005/0180699 A1 | | 8/2005 | Shu et al. |

FOREIGN PATENT DOCUMENTS

| | | |
|---|---|---|
| EP | 0 638 770 A1 | 2/1995 |
| EP | 0 816 760 A1 | 1/1998 |
| JP | 08-68573 * | 3/1996 |
| WO | WO 99/30006 | 6/1999 |

OTHER PUBLICATIONS

Hoff, et al., Closed-Loop Combustion Control using OH Radical Emissions, Proceedings of ASME TURBOEXPO 2000, May 8-11, 2000, Munich Germany.
Natural Gas Fuel for General Electric Aircraft Derivative Gas Turbines in Industrial Applications, General Electric Company Marine & Industrial Engine Projects Department, Cincinnati, Ohio 45215, MID-TD-0001-1, Aug. 1985.
European Search Report published Jul. 13, 2005.
European Search Report dated Jan. 16, 2007.

* cited by examiner

*Primary Examiner*—L. J. Casaregola
(74) *Attorney, Agent, or Firm*—Scott D. Wofsy; Edwards Angell Palmer & Dodge LLP

(57) ABSTRACT

A fuel injector for a gas turbine combustor is disclosed which includes a feed arm having a flange for mounting the injector within the combustor and a fuel nozzle depending from the feed arm for injecting fuel into the combustor for combustion. An optical sensor array is located within the fuel nozzle for observing combustion conditions within the combustor.

33 Claims, 7 Drawing Sheets

APPARATUS, SYSTEM AND METHOD FOR OBSERVING COMBUSTION CONDITIONS IN A GAS TURBINE ENGINE

BACKGROUND OF THE INVENTION

1. Field of the Invention

The subject invention is directed to optical sensors for gas turbine engines, and more particularly, to an apparatus, system and method for observing the spectral and thermal characteristics of a flame in the combustion chamber of a gas turbine engine to detect, in real-time, conditions indicative of combustion instabilities and the like.

2. Background of the Related Art

Combustion instability is a significant problem in the design of low-emission, high performing combustion chambers for gas turbines, boilers, heaters and furnaces. Combustion instability is generally understood as high amplitude pressure oscillations that occur as a result of the turbulent nature of a combustion process and the large volumetric energy release within the combustion chamber. Combustion instability diminishes engine system performance, and the vibrations resulting from pressure oscillations can damage hardware components, including the combustion chamber.

There are many factors that contribute to combustion instability within the combustion chamber of a gas turbine. These include, for example, the fuel content, fuel and/or air injection speed or inlet pressure, fuel/air concentration/ratio, temperature changes within the combustion chamber, the stability of the flame, large scale coherent flow structures affecting mixing (i.e., vortex shedding), the coupling of acoustic pressure waves with combustion heat release at combustor resonance frequencies, and/or extinction/re-ignition phenomenon occurring at low flame temperature and high combustion pressure.

In the past, passive control methods were employed to correct combustion instability, including, for example, modifying the fuel injection distribution pattern, or changing the shape or capacity of the combustion chamber. Passive controls are often costly and limit combustor performance. More recently, active controls have been used to correct combustion instability by modifying the pressure within the system and/or regulating the flow of fuel or air into the combustor in response to detected unstable conditions. An example of active control is disclosed in U.S. Pat. No. 5,784,300 to Neumeier et al.

It has been determined through experimentation that direct observation of a combustor flame can provide information that may be used to actively control combustion instability. For example, combustion driven pressure oscillations can be detected by observing flame movement and variations in flame intensity. In addition, spectral radiation indicative of combustion by-products and emissions that effect flame temperature or other flame qualities may be observed. These observations may be analyzed and used by an active combustion control system to regulate the flow of fuel to the combustion chamber of a gas turbine or adjust the fuel/air ratio for combustion and thereby stabilize the combustion process.

Optical sensors for observing combustion processes are known in the prior art, but they are limited in many respects. For example, U.S. Pat. No. 3,689,773 to Wheeler describes a flame monitoring system for a furnace wherein the flame is viewed from the side of the burner. Since the primary combustion zone within the burner is not stationary, the flame front can move out of the field of vision of the flame sensor. This can cause the system to obtain inaccurate measurements. U.S. Pat. No. 4,709,155 to Yamaguchi et al. describes an optical flame detector for use in a boiler that includes optical fibers protected from thermal damage by a forced air-cooling system. Such a system would have limited application in a gas turbine combustor where operating temperatures are far in excess of those present in a boiler.

Clearly, there is a need in the art for an optical flame sensor that may be used in active combustion control which overcomes the deficiencies of prior art optical flame sensors. Moreover, there is a need in the art for an optical flame sensor that may be employed in the combustion chamber of a gas turbine engine, which has a wide field of view so that the combustor flame will remain within the line of sight of the sensor at all times during the combustion process, and which does not require cooling means to operate within the combustion chamber.

SUMMARY OF THE INVENTION

The subject invention is directed to an apparatus for observing conditions within the combustion chamber of a gas turbine engine. More particularly, the subject invention is directed to a new and useful fuel injector for a gas turbine engine that includes, among other things, optical sensing means for observing characteristics of the combustor flame. Specifically, the optical sensing means is configured to detect spectral and thermal conditions that destabilize the combustion process.

The fuel injector of the subject invention includes an elongated feed arm having means for mounting the injector within the combustion chamber, such as a flange for securing the injector to the interior wall or liner of the combustor. The fuel injector further includes a fuel nozzle or nozzle body, which depends from the feed arm for injecting or otherwise issuing atomized fuel into the combustion chamber for combustion. In accordance with a preferred embodiment of the subject invention, optical sensing means are provided within the fuel nozzle for observing combustion conditions within the combustion chamber, downstream from the fuel nozzle.

In accordance with a preferred embodiment of the subject invention, the fuel nozzle includes an outer air swirler having a leading edge. A plurality of circumferentially spaced apart viewing ports are formed in the leading edge of the outer air swirler. For example, the leading edge of the outer swirler can include three or more viewing ports spaced equidistant from one another. Preferably, the optical sensing means of the subject invention includes a plurality of optical fiber bundles, and there is an optical fiber bundle accommodated within each of the viewing ports formed in the outer swirler. In addition, the optical sensing means may further include one or more optical fibers mounted or otherwise supported within a holder along the central axis of the fuel nozzle.

It is envisioned that each embedded optical fiber bundle has a field of view of between about 14° to 30° (dependent on the fiber Numerical Aperture) relative to axis of fiber. Each optical fiber bundle preferably includes a plurality of optical fibers, and these optical fibers are oriented so as to extend substantially parallel to the central axis of the fuel nozzle. The optical fibers are preferably treated to withstand the operating temperatures within the combustor. For example, the optical fibers may be provided with a metal coating, such as gold or another precious metal, well suited for thermal protection.

Each optical fiber bundle is preferably disposed within a temperature resistant guide tube. For example, the fiber bundles may be disposed within stainless steel guide tubes. Preferably, the distal end of each stainless steel guide tube is cemented within a corresponding viewing port in the outer air swirler of the fuel nozzle in a manner that accommodates thermal expansion and contraction. This will serve to maintain the structural integrity of the system through a multitude of engine operating cycles.

The subject invention is further directed to a system for stabilizing combustion in a gas turbine engine by observing conditions within the combustion chamber. The system includes, among other things, optical sensing means, preferably embedded within each fuel injector, for observing conditions within the combustion chamber, means for detecting combustion instabilities based upon conditions observed by the optical sensing means, and means for modulating the rate of fuel flow to the combustion chamber to reduce the detected combustion instabilities or otherwise stabilize combustion.

In accordance with a preferred embodiment of the subject invention, the means for detecting combustion instabilities is adapted and configured to analyze and process information relating to combustor flame characteristics, including thermal and spectral conditions. For example, the means for detecting combustion instabilities may include means for detecting changes in flame intensity at levels indicative of flame instability.

Alternatively, the means for detecting combustion instabilities may include means for detecting spectral radiation indicative of stoichiometric instability. In one embodiment of the subject invention, the detecting means is configured to detect and analyze spectral radiation indicative of chemical emissions effecting flame temperature, NOx, CO, fuel/air ratio and equivalence ratio. It is also envisioned that the detecting means can be employed in turbine engines fueled by natural gas. In such instances, the detecting means is configured to detect variability in the natural gas composition that will affect fuel heat values. For example, the detecting means could be configured to detect spectral variations relating to ethane, propane, nitrogen and carbon dioxide. The system could also be configured to detect the presence of natural gas contaminants, such as sodium, which can have a corrosive effect on hot engine parts.

The subject invention is also directed to a method of promoting stable combustion in a gas turbine engine. The method includes the steps of observing a combustor flame from a location upstream from the flame to detect spectral characteristics indicative of one or more conditions affecting combustion stability, and subsequently tuning the engine to stabilize combustion based upon an indicated condition effecting combustion stability. In one embodiment of the subject invention, the step of observing a combustor flame includes the step of detecting changes in spectral intensity indicative of flame instability. In another embodiment of the subject invention, the step of observing a combustor flame includes the step of detecting spectral radiation peaks or emissions indicative of stoichiometric instability. Those skilled in the art will readily appreciate that the step of tuning the engine to stabilize combustion includes adjusting the fuel flow and/or air flow to the combustion chamber, or otherwise the fuel to air ratio for combustion.

These and other aspects of the apparatus, system and method of the subject invention will become more readily apparent to those having ordinary skill in the art from the following detailed description of the invention taken in conjunction with the drawings.

BRIEF DESCRIPTION OF THE DRAWINGS

So that those having ordinary skill in the art to which the present invention pertains will more readily understand how to employ the novel apparatus, system and method of the present invention, embodiments thereof will be described in detail hereinbelow with reference to the drawings, wherein.

DETAILED DESCRIPTION OF THE PREFERRED EMBODIMENTS

Figure 1:
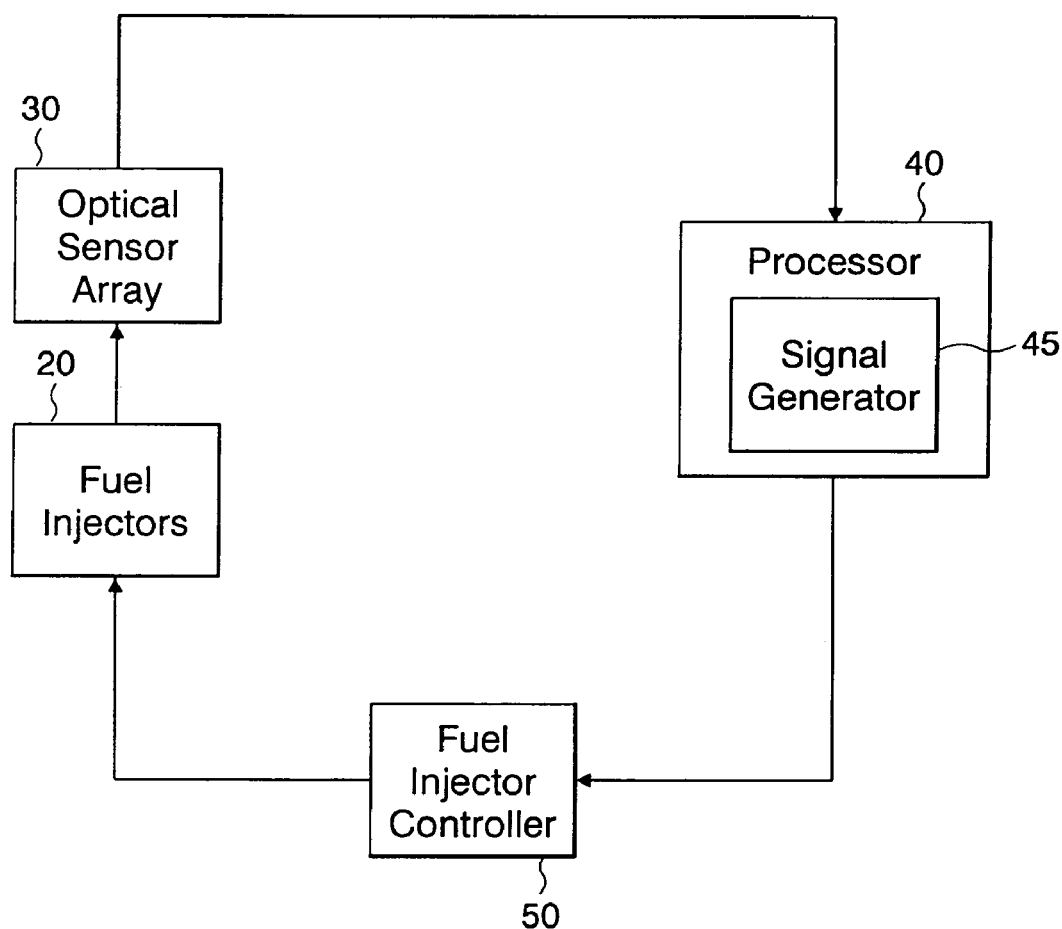
FIG. 1 is a schematic representation of an active combustion control system for a gas turbine engine configured in accordance with a preferred embodiment of the subject invention.

Referring now to the drawings wherein like reference numerals identify similar features or aspects of the subject invention, there is illustrated in FIG. 1 an active combustion control system configured in accordance with a preferred embodiment of the subject invention, and designated generally by reference numeral 10. The active combustion control system 10 is designed to reduce thermo-acoustic combustion instabilities within the combustion chamber of a gas turbine engine. The system is intended to lower engine emissions, improve engine dynamics and maximize operating efficiency. The active combustion control system of the subject invention is particularly well suited for use in combustion systems that are inherently unstable such as, for example, industrial gas turbine engines wherein lean premixed combustion is used to reduce NOx, and high power thrust augmented military aircraft engines (afterburners) which utilize locally rich combustion.

Referring to FIG. 1, active combustion control system 10 includes a plurality of fuel injectors 20, described in detail below, which deliver atomized fuel to the combustion chamber of a gas turbine engine at a controlled rate of flow. There are two primary types of atomizing fuel injectors, and either type of injector may be employed with the system of the subject invention. These devices include swirl pressure atomizers, which derive energy for atomization from fuel pressure, and air blast atomizers, which derive energy for atomization from high velocity compressor air. Examples of atomizing fuel injectors are disclosed in U.S. Pat. No. 6,688,534 to Bretz, the disclosure of which is incorporated herein by reference in its entirety.

The fuel injectors 20 each include a plurality of optical sensors 30 in the form of an array for observing conditions within the combustion chamber of a gas turbine engine, such as, for example, the thermal and spectral stability of the combustor flame. These optical sensors 30 are embedded in or otherwise integral with the fuel injectors 20, and are well adapted for prolonged service within the highly corrosive, high temperature environment of a gas turbine combustion chamber, as will be described in greater detail below.

The active combustion control system 10 of the subject invention further includes an electronic signal processor 40. Signal processor 40 is adapted and configured to analyze and process real-time data received from or otherwise transmitted by the optical sensor array 30 associated with each of the fuel injectors 20. This real-time optical data is primarily used to detect combustion instability within the combustion chamber of the gas turbine engine, including conditions relating to spectral and/or thermal stability.

Preferably, the signal processor 40 includes a signal-generating device 45, which generates output signals based upon the data received from the optical sensors 30. The signal generator 45 is preferably filtered so as to acquire energy in a narrow spectral band relating to an emission from a specific chemical species or radical. Alternatively, it is envisioned that the signal generator could be filtered in such a manner so as to acquire energy is a plurality of specific spectral bands, each of which relates to an emission from specific chemical species or radical.

In one embodiment of the invention, the signal processor 40 may include one or more filtered photo multiplier tubes (PMT) for electronically amplifying a light signal. For example, the signal processor can include eight different filtered PMT's. Alternatively, signal processor 40 may include one or more filtered silicone photodiodes each with an integral operational amplifier.

A photodiode is a solid-state device that detects light and creates a current flow between doped forms of silicon in response thereto. In comparison, the sensitivity of a PMT may be adjusted and it provides a faster response than a photodiode. Furthermore, PMT's are designed to detect relatively weak signals as compared to photodiodes. However, photodiodes are cheaper, more robust and more readily available in a wider variety of wavelengths than PMT's. Nevertheless, these types of signal generators are considered to be interchangeable and both provide reliable output signals for detecting conditions effecting combustion stability. The type of signal generator employed will depend upon the signal strength, wavelengths to be detected and cost.

The output signal generated by signal processor 40 undergoes an analysis to detect conditions effecting spectral and/or thermal instability, which are root causes of combustion instabilities. The analysis is performed by a computer-based spectrometer, which is operatively associated with the signal processor 40. A suitable spectrometer preferably has a range of between 180 and 800 nm, and is programmed or otherwise configured to derive flame quality parameters relating to combustion stability, such as flame stability and flame temperature, as well as the presence of fuel contaminants, fuel components and chemical emissions or radicals.

Figure 2:
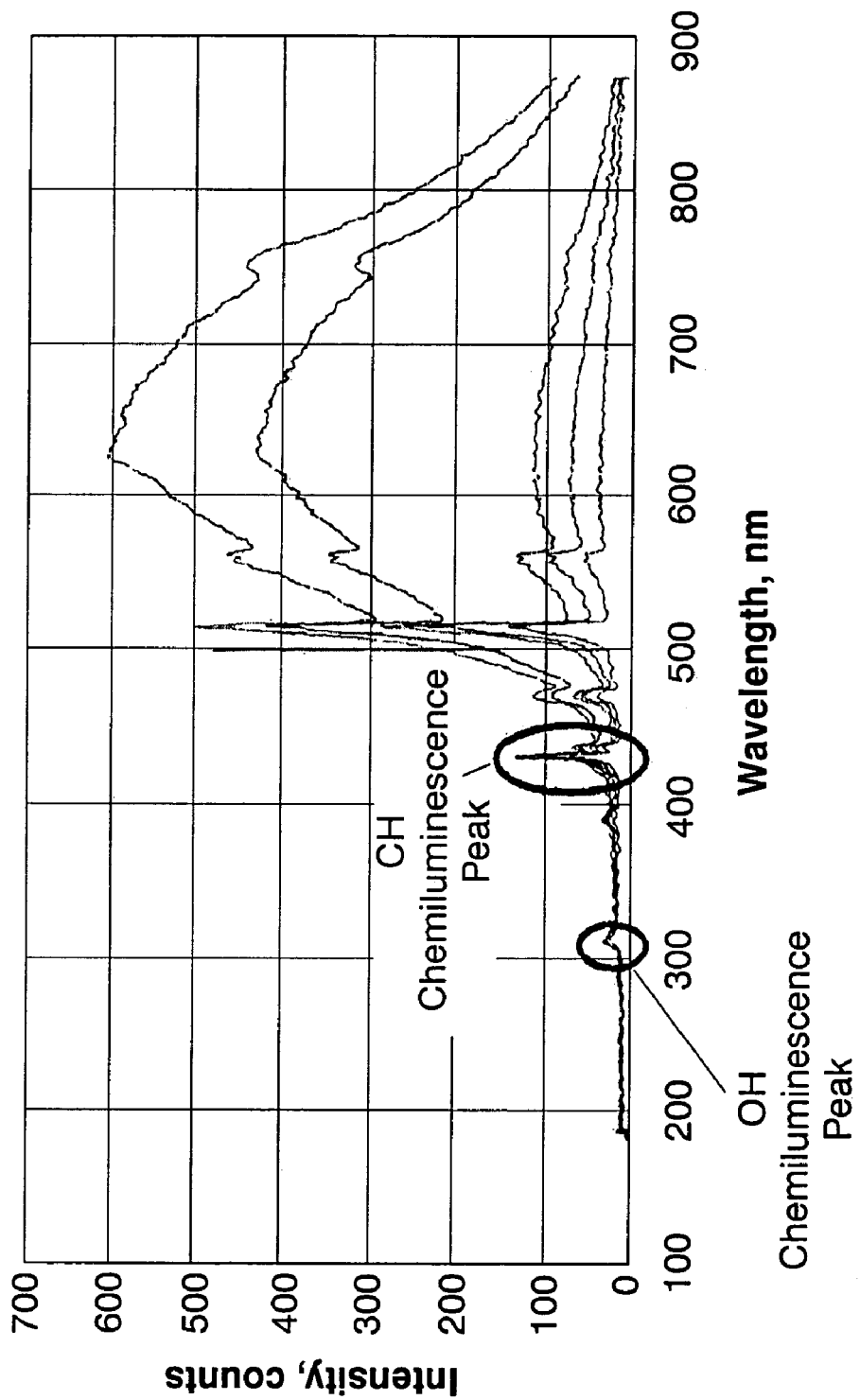
FIG. 2 is a graphical illustration of a spectral scan generated by a computer based spectrometer using optical data obtained by observing conditions within the combustion chamber of a gas turbine engine utilizing the optical sensing array of the subject invention.

In one embodiment of the subject invention, the signal processor 40 and associated spectrometer are programmed or otherwise configured to detect and analyze changes in flame intensity. These changes are indicative of the combustion driven pressure oscillations, which cause combustion instability in a gas turbine engine. It is envisioned that the optical sensor array 30 and/or signal processor 40 would be calibrated under normal engine operating conditions, so that variations in optical intensity or optical signal amplitude with respect to the variations in the intensity of the instability would be evaluated based upon calibrated values. A spectral scan generated with the optical sensor array 30 of the subject invention and depicting variations in spectral intensity with changes in fuel to air ratios is illustrated in FIG. 2. Upon detecting variations in spectral intensity indicative of an unstable operating condition, the fuel flow rate could be adjusted or modulated to stabilize combustion.

In another embodiment of the subject invention, the signal processor 40 and associated spectrometer are configured to detect spectral radiation indicative of chemical emissions effecting combustion stability. More particularly, signal processor 40 is programmed to detect and analyze the ratio of OH chemiluminescence peaks (occurring at about 310 nm) and CH chemiluminescence peaks (occurring at about 430 nm) observed by optical sensor array 30, as illustrated in FIG. 2. This information is then correlated to the flame temperature, NOx, CO, fuel/air ratio or equivalence ratio. This emissions feedback is then used to tune the engine to a stable operating condition, such as by adjusting the fuel flow, air flow and/or fuel to air ratio for combustion.

In yet another embodiment of the subject invention, the signal processor 40 and associated spectrometer are programmed or otherwise configured to detect and analyze spectral radiation indicative of fuel contaminants or impurities effecting fuel heat values. This is of particular importance in turbine engines powered by natural gas, since natural gas is typically an unpurified fuel. It is well known that variability in the composition of natural gas can affect fuel heat values. For example, variations in the amount of ethane, propane, nitrogen and carbon dioxide can cause heat value to vary. It is also known that the presence of sodium in natural gas can have a corrosive affect on hot engine parts such as the combustor itself and turbine blades. Changes in fuel heat values can cause a gas turbine engine powered by natural gas to become de-tuned and can jeopardize the stability of the combustion process. Upon detecting spectral emissions or radicals indicative of the presence of certain fuel contaminants or impurities, the engine can be tuned to a stable operating condition.

With continuing reference to FIG. 1, the signal processor 40 is operatively associated or otherwise in communication with a fuel injector controller 50. The fuel injector controller 50 is adapted and configured to receive a conditioned signal from processor 40. Based on this signal, the fuel injector controller 50 commands or otherwise controls the flow of fuel to each of the fuel injectors 20 to reduce or otherwise correct a detected condition effecting combustion stability. For example, the fuel controller 50 could command a pulsed or modulated fuel flow to the fuel injectors to stabilize combustion. Alternatively, fuel controller 50 could be configured to adjust the fuel to air ratio/concentration for combustion.

Figure 3:
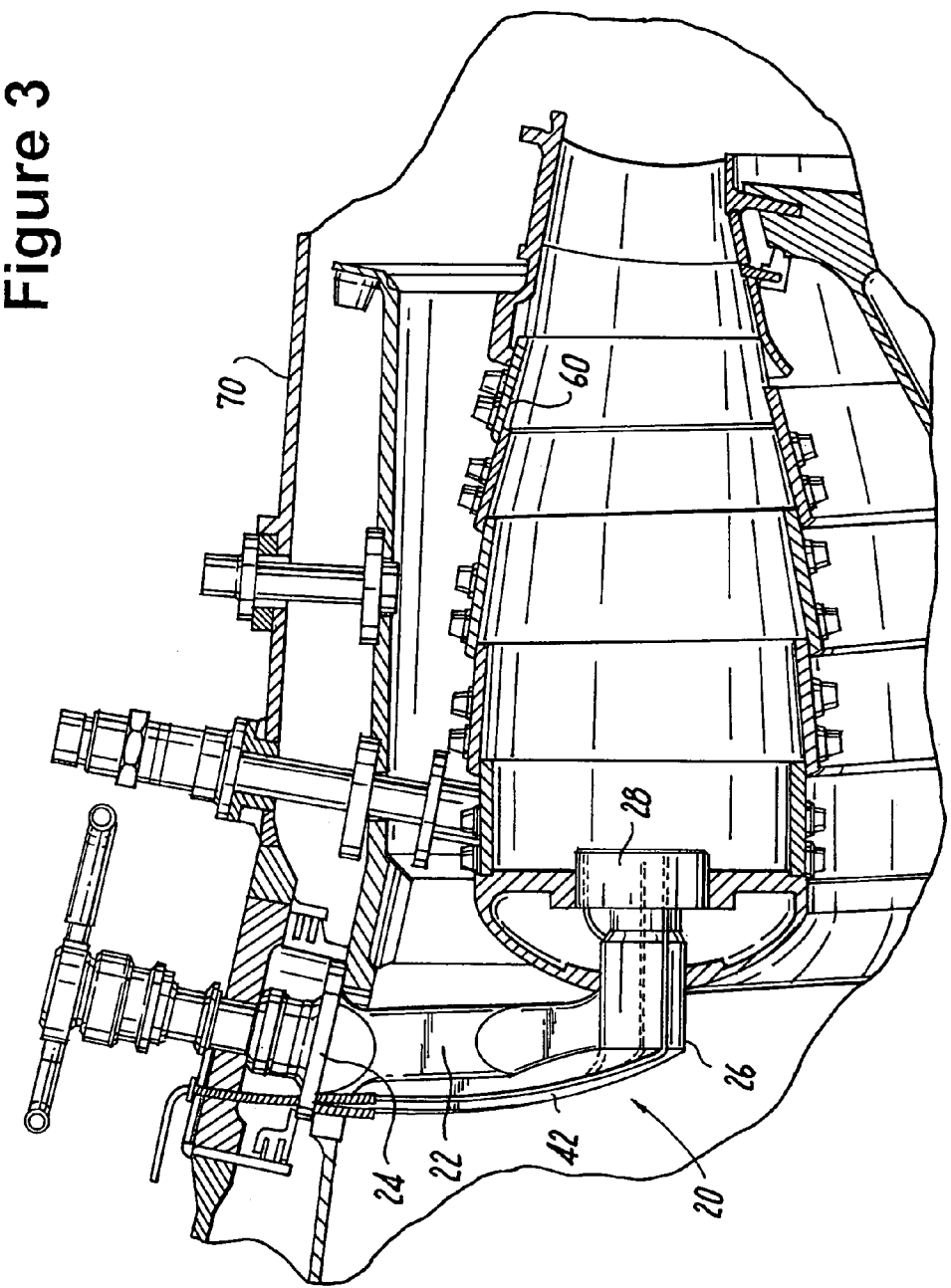
FIG. 3 is a side elevational view, in cross-section, of the combustion chamber of a conventional gas turbine engine, which includes fuel injectors containing the optical sensing array of the subject invention.
Figure 4:
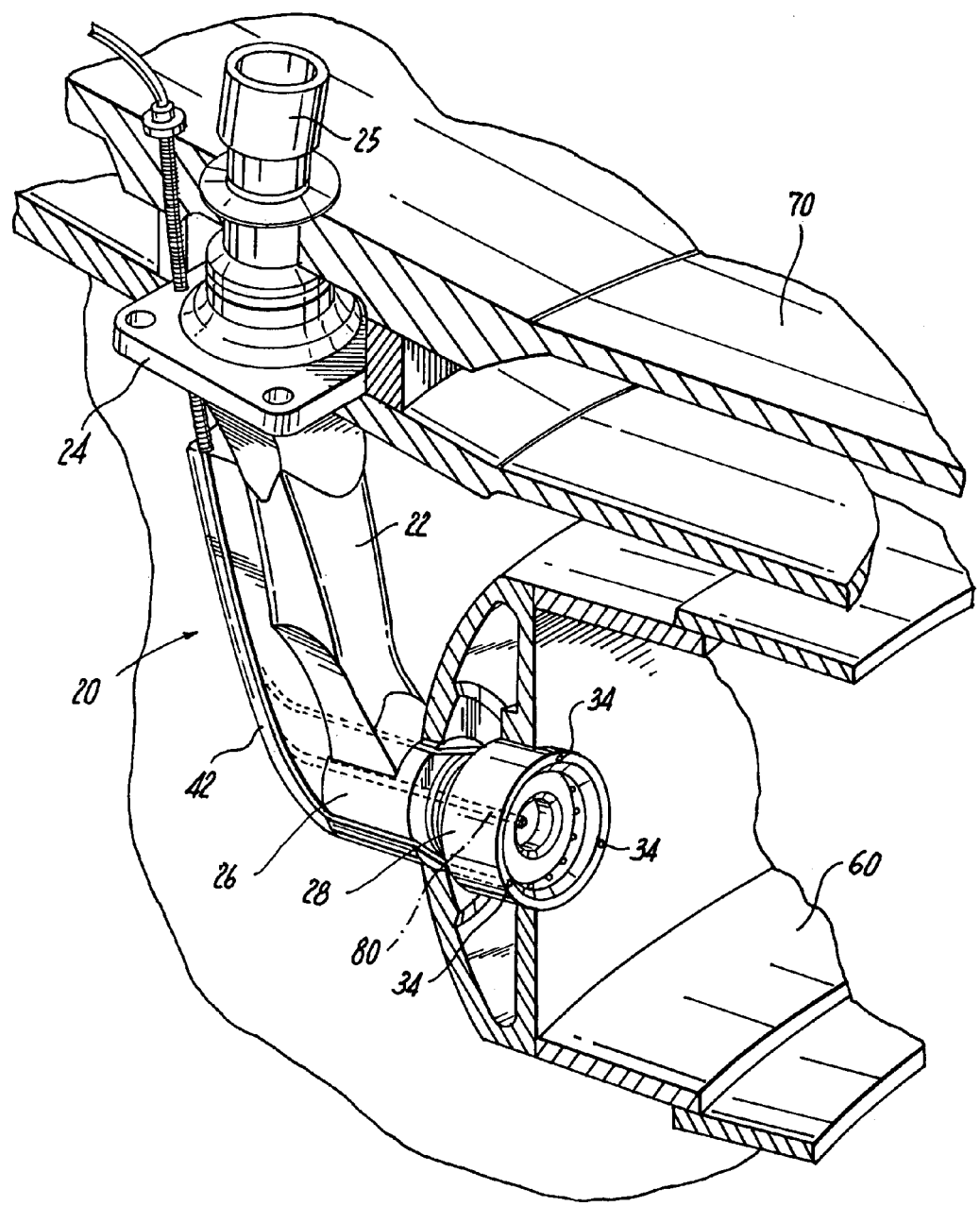
FIG. 4 is a perspective view of a fuel injector constructed in accordance with a preferred embodiment of the subject invention, located within the combustion chamber of a gas turbine.

Referring now to FIGS. 3 and 4, the fuel injectors 20 of the subject invention are mounted or otherwise supported within the combustion chamber 60 of gas turbine engine 70 in a conventional manner. More particularly, each fuel injector 20 includes an elongated feed arm 22 having a support flange 24 for mounting the injector within the combustion chamber 60. The support flange 24 is particularly adapted to secure the injector to the interior wall or liner of the combustion chamber using conventional fasteners. The fuel injector 20 further includes an inlet port 25 for receiving fuel from a fuel pump at a desired flow rate. A fixed or variable displacement vane pump may be employed. A fuel nozzle 26 depends from the distal end of feed arm 22 and is designed to inject or otherwise issue atomized fuel into the combustion chamber 60. As noted above, a fuel injector 20 can take the form of a pressure atomizer or an air blast atomizer. In either configuration, the fuel nozzle 26 includes an outer air swirler 28 configured to impart an angular component of velocity to the air flowing through the nozzle body.

Figure 5:
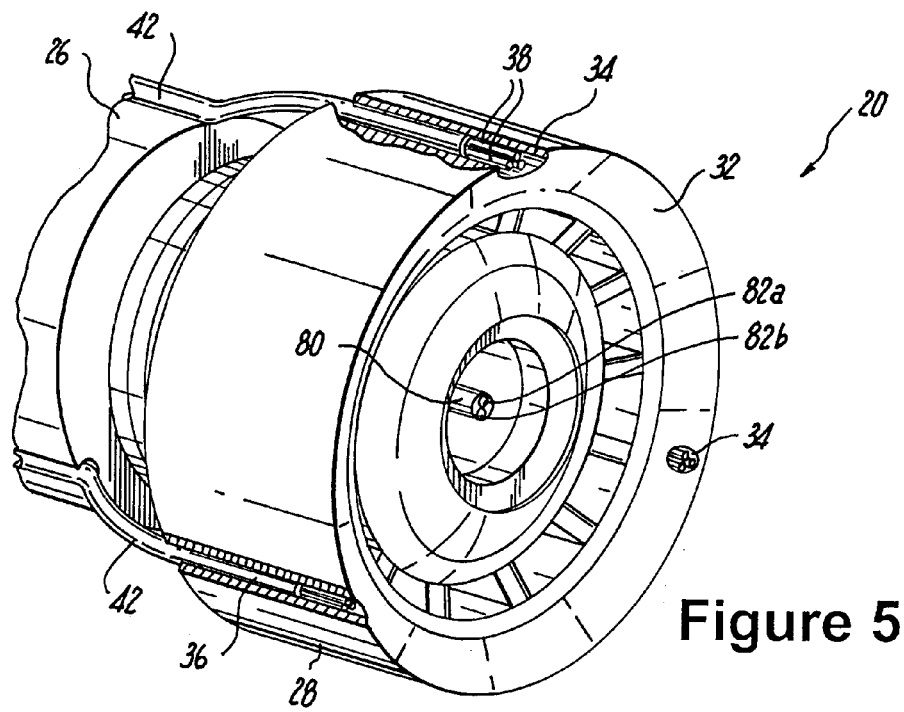
FIG. 5 is an enlarged perspective view of the fuel nozzle, which forms part of the fuel injector of FIG. 4, with sections of the outer air swirler removed to reveal the optical fiber bundles for viewing conditions within the combustion chamber.
Figure 6:
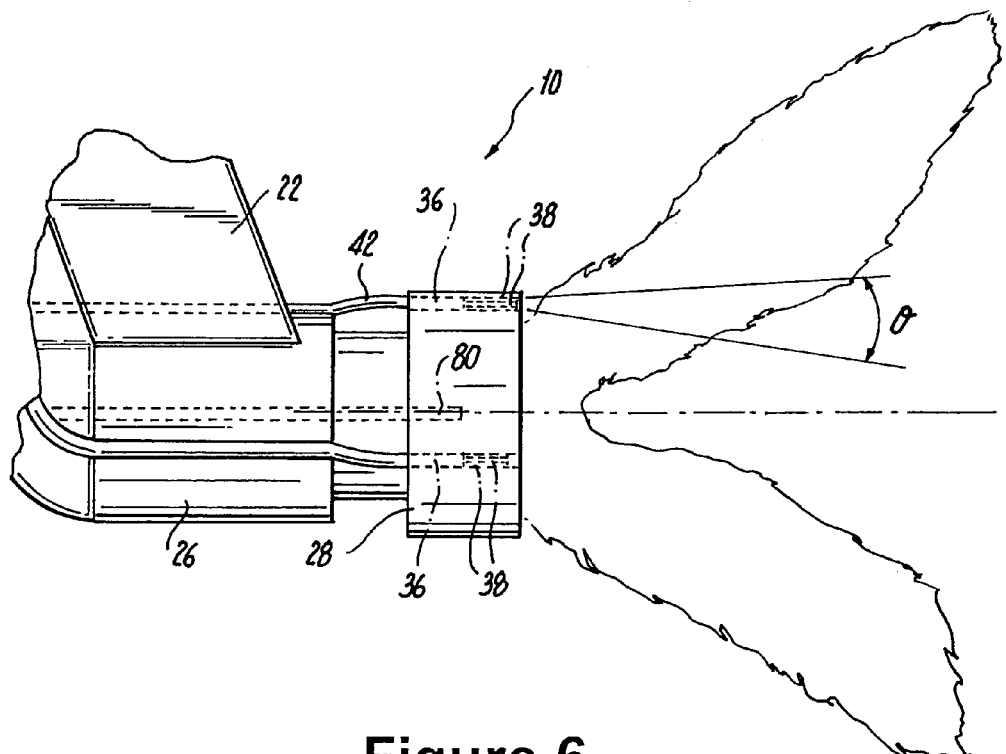
FIG. 6 is a side elevational view of the lower portion of the fuel injector of FIG. 4 depicting the field of view of the fiber bundles embedded within the fuel nozzle.

Referring now to FIGS. 5 and 6, in accordance with a preferred embodiment of the subject invention, the optical sensors 30 described briefly above are provided, located or otherwise embedded within the outer air swirler 28 of fuel nozzle 26 for observing combustion conditions within the combustion chamber 60 of gas turbine 70, downstream from the fuel nozzle. To accommodate the optical sensors 30 in a non-intrusive manner, a plurality of circumferentially spaced apart viewing ports are formed in the leading edge 32 of the outer air swirler 28, creating an optical sensor array. For example, as best seen in FIG. 4, the leading edge 32 of the outer swirler 28 can include three viewing ports 34, which are preferably spaced substantially equidistant from one another (e.g., about 120° apart), and an optical sensor 30 is accommodated within each viewing port 34.

Those skilled in the art will readily appreciate that the number of viewing ports formed in the outer air swirler 28 of the fuel nozzle 26 can vary from one nozzle type to another, and/or from one engine type to another. For example, four viewing ports spaced 90° apart from one another can be provided in a particular nozzle body constructed in accordance with the subject invention. It should also be understood by those skilled in the art that the optical sensors disclosed herein can be embedded in other parts of the nozzle body, other than the outer air swirler, without departing from the spirit or scope of the subject invention. That is, depending upon the type and structure of the nozzle body, the location of the embedded sensors can vary, so long as they have an adequate field of view downstream from the fuel nozzle, and remain non-obtrusive in that they do not negatively affect the overall performance of the fuel nozzle.

It has been found through experimentation that disposing the optical sensors 30 at the leading edge 32 of the fuel nozzle 26 is advantageous, since the combustor flame will remain within the line of sight or field of view sensors, thus providing a fairly accurate representative map of the flame zone. It has also been found that positioning the optical sensors 30 at a plurality of spaced apart locations around the leading edge 32 of the fuel nozzle 26, thus forming an optical sensor array, will allow specific modes of combustion instability to be observed and determined. By knowing the specific form of the instability, more effective control can be achieved.

The optical sensors 30 are defined, in pertinent part, by optical fiber bundles 36. An optical fiber bundle 36 consists of a plurality of individual optical fibers 38. This provides redundancy in case of failure, more efficient energy transfer to the signal processor 40, and allows for a broader field of view relative to the combustor flame. In addition, an optical fiber bundle is easily bent to accommodate contours of the fuel nozzle.

It is envisioned that each optical fiber bundle 36 has a field of view defined by angle θ of between about 14° and 30° relative to axis of fiber, as best seen in FIG. 6. It is also envisioned that the optical fiber bundles 36 can be split or otherwise configured such that individual fibers within each bundle will observe different spectral wavelengths within their field of view.

In one embodiment of the subject invention, each optical fiber bundle 36 includes three individual optical fibers 38. The optical fibers 38 are aimed or otherwise oriented so as to extend generally parallel to the central axis of the fuel nozzle 26, as best seen in FIGS. 4 and 5. It has been determined that this orientation provides the broadest field of view with respect to the combustor flame. Those skilled in the art will readily appreciate however, that the specific orientation of the fiber bundles can vary depending, for example, upon the geometry of the fuel nozzle.

The optical fibers 38 forming fiber bundles 36 can consist of 100μ silica (UV enhanced) fibers or the like. The fibers 38 are preferably coated or otherwise treated to withstand the operating temperatures within the combustion chamber 60. These temperatures can exceed 500° C. For example, the optical fibers 38 may be provided with a coating, such as gold or a similar precious metal suited for thermal protection. Other coatings resistant to high temperatures may also be used.

Each optical fiber bundle 36 is disposed within a temperature resistant guide tube 42 for additional thermal protection. For example, the fiber bundles 36 may be disposed within stainless steel guide tubes or a similar protective structure. The distal end of each guide tube 42 is swaged to secure the fibers therein, and cemented within a corresponding viewing port 34 in a manner that accommodates thermal expansion and contraction. For example, ceramic cement may be used to secure the distal end of each guide tube 42 within a viewing port 34. This will ensure the integrity of the fiber bundles throughout a multiplicity of engine operating cycles. The guide tubes 42 are preferably embedded in or otherwise mounted to the feed arm 22 of fuel injector 20. For example, the guide tubes may be positioned within channels formed in the feed arm 22 of fuel nozzle 20. The proximal end of each fiber bundle 36 terminates at a location external to the combustion chamber 60 in a conventional optical connector (not shown), which is suitable for reception by signal processor 40.

Referring to FIG. 5, in addition to the plurality of optical fiber bundles 36 positioned within the viewing ports 34 formed in the outer air swirler 28 of the fuel nozzle 26, an optical sensor 80 may be mounted along the central axis of fuel nozzle 26 to increase the overall field of view and functionality of the system. Optical sensor 80 can consist of one or more coated optical fibers. For example, optical sensor 80 can consist of one or more gold-coated 400μ silica (UV enhanced) fibers or the like.

Figure 7:
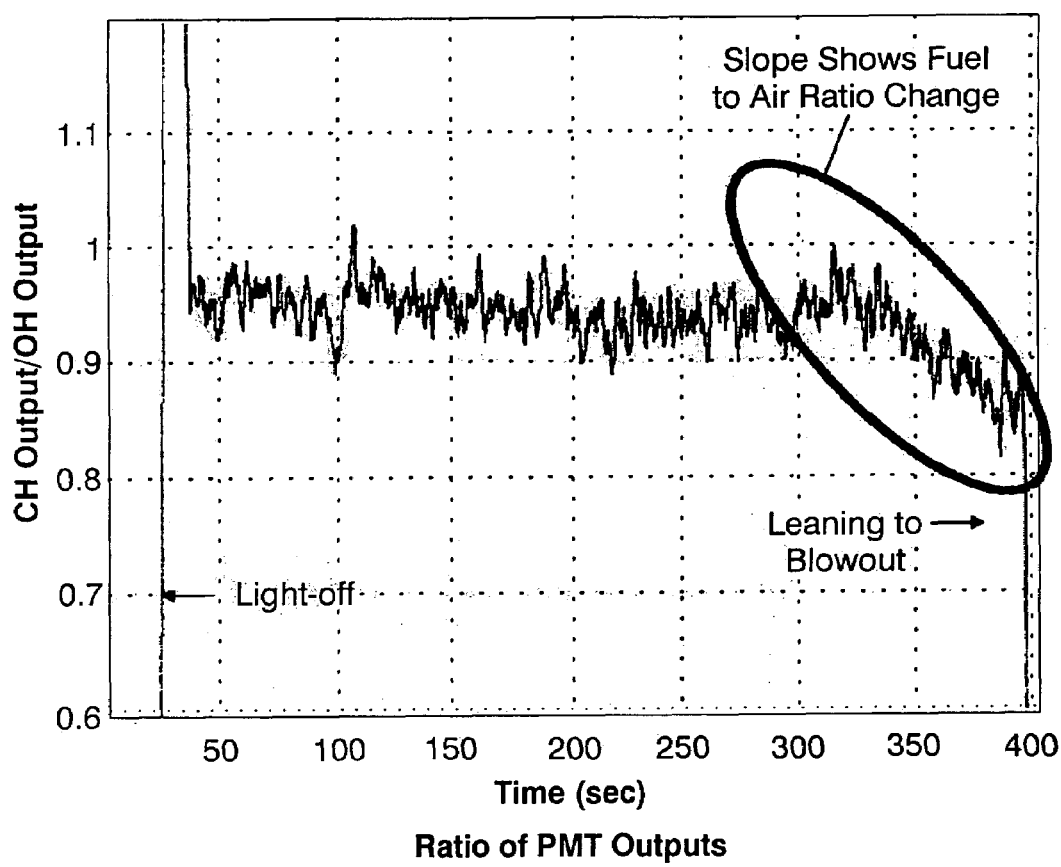
FIG. 7 is a graphical illustration of a spectral ratio scan generated by a computer based spectrometer using optical data obtained by a pair of optical fibers located centrally within the fuel injector nozzle of the subject invention.

In one embodiment of the subject invention, optical sensor 80 is axially mounted within the fuel nozzle 26 by a supporting fixture associated with the inner air swirler (not shown). In this position, sensor 80 is utilized to detect variations in spectral ratios indicative of stoichiometric stability. More particularly, in such an embodiment, optical sensor 80 includes two optical fibers 82a, 82b that are axially positioned in side-by-side relationship to detect variations in spectral ratios of CH output to OH output generated over a period of time by the signal generator of signal processor 40. For example, as illustrated in the spectral scan of FIG. 7, the relationship of the CH output signal to the OH output signal over time, generated by corresponding PMT's of signal generator 40, can be correlated to changes in fuel to air ratio. Based on this information, the engine will be tuned to stabilize combustion. In another embodiment of the subject invention, the axially mounted optical sensor can include two optical fiber bundles, each containing four gold-coated 200µ silica fibers rated to 700° C.

In accordance with another embodiment of the subject invention, the optical sensor array 30 of fuel injector 20 is adapted and configured to detect radiation in the infrared spectrum. In this case, the sensor array is embedded in the fuel nozzle 26 in the same manner described and illustrated above, but one or more of the optical fibers 38 are IR enhanced instead of UV enhanced. In one embodiment, the IR enhanced optical fibers 38 are adapted and configured to detect spectral radiation in the 1.7µ to 2.1µ range. This correlates to exhaust gas temperature. In contrast, exhaust gas temperature does not correlate to the chemiluminescence outputs in the UV range described previously.

It has been determined that there is an absorption/emission band for water vapor generated by the combustion process within the 1.7µ to 2.1µ range. It is envisioned that the output from the infrared sensor array may be used to obtain flame temperature, in a manner similar to an optical pyrometer. It is also envisioned that the output from the infrared sensor array may be used to obtain turbine inlet vane temperature when in the field of view.

Figure 8A:
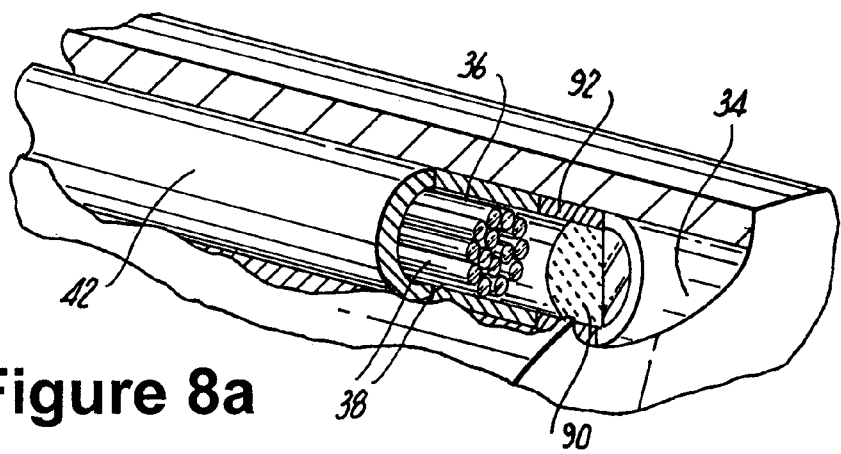
FIGS. 8a through 8c illustrate three different methods of terminating an optical fiber bundle in accordance with the subject invention.
Figure 8B:
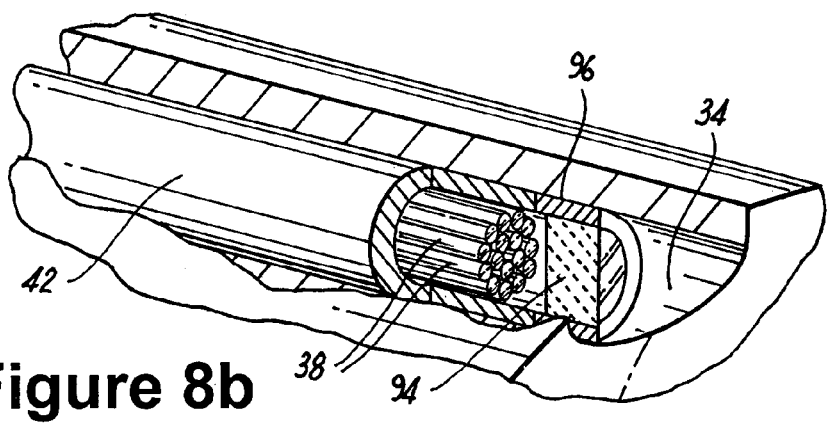
Figure 8C:
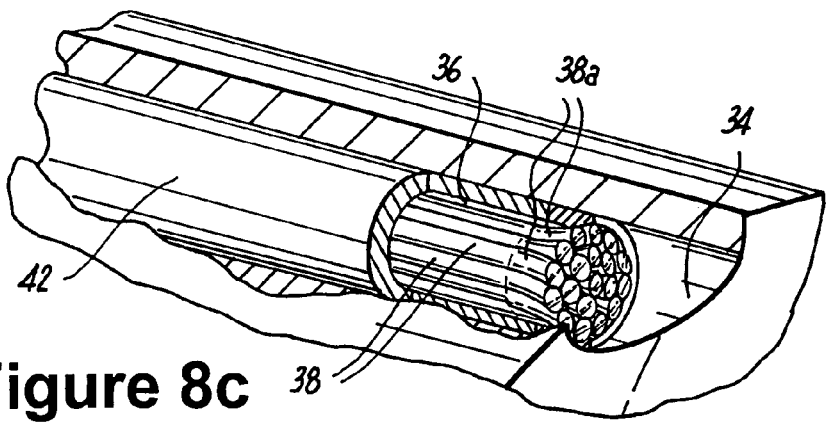

Referring now to FIGS. 8a through 8c, there are illustrated three different methods of terminating the optical fibers 38, which form the fiber bundles 36 within the stainless steel guide tubes 42 located in view ports 34. In one embodiment shown in FIG. 8a, the optical fibers 38 terminate at a location spaced from the distal end of the guide tube 42. A shaped lens 90 supported within a frame 92 is joined to the distal end of the guide tube 42. The lens 90 is formed from a material such a sapphire and is used to focus or otherwise modify the field of view of the optical fibers 38. It is envisioned that the exposed surface of the lens 90 would have a protective coating. For example, the lens can have a vapor deposited layer comprising a mixture of platinum and aluminum oxide which acts as a catalyst to promote oxidation of soot to a gaseous form and thereby reduce contamination of the lens, as disclosed in U.S. Pat. No. 4,521,088 to Masom, the disclosure of which is incorporated herein by reference in its entirety.

In another embodiment shown in FIG. 8b, the optical fibers 38 terminate at a location spaced from the distal end of the guide tube 42, and a window 94 supported within a frame 96 is joined to the distal end of the guide tube 42. The window 94 may be formed from sapphire or a similar transparent material and would function to seal the end of the guide tube from contamination and combustion by-products, which could degrade the optical fibers. It is envisioned that the window 94 could also be frosted or otherwise treated and used as a diffuser to widen the viewing area of the optical fiber bundle.

In the embodiment shown in FIG. 8c, the distal ends 38a of each optical fiber 38 in fiber bundle 36 is splayed or otherwise spread outwardly so that each individual fiber end 38a is oriented or directed in a different direction relative to the axis of the bundle. This enables the optical fibers to gather light from a broader or greater area. Protective coatings could be used to coat the ends of the fibers.

In sum, the fiber optic instrumented fuel injector of the subject invention may be used for a multiplicity of purposes including, for example, engine control through detection of combustion instability; fuel to air ratio stability by analyzing spectral relationships; obtaining turbine inlet temperature correlated to flame temperature; detection of fuel impurities based on spectral anomalies; aircraft augmenter flame detection; obtaining turbine inlet vane temperature by way of a pyrometer; and advanced warning or prediction of lean blowout conditions.

Although the apparatus, system and method of the subject invention have been described with respect to preferred embodiments, those skilled in the art will readily appreciate that changes and modifications may be made thereto without departing from the spirit and scope of the subject invention as defined by the appended claims.

What is claimed is:

1. A fuel injector for a gas turbine combustor, comprising:
   a) a feed arm including means for mounting the injector within the combustor;
   b) a fuel nozzle depending from the feed arm for injecting fuel into the combustor for combustion, wherein the fuel nozzle includes a leading edge having a plurality of spaced apart viewing ports formed therein; and
   c) optical sensing means embedded in the viewing ports of the fuel nozzle for observing combustion conditions within the combustor.

2. A fuel injector as recited in claim 1, wherein the fuel nozzle has a central axis and includes an outer swirler, wherein the outer swirler includes the leading edge of the fuel nozzle, and wherein the plurality of spaced apart viewing ports are located around the leading edge of the outer swirler.

3. A fuel injector as recited in claim 2, wherein the leading edge of the outer swirler includes three viewing ports spaced equidistant from one another.

4. A fuel injector as recited in claim 2, wherein the optical sensing means includes a plurality of optical fiber bundles, and wherein an optical fiber bundle is accommodated within each viewing port.

5. A fuel injector as recited in claim 4, wherein each optical fiber bundle includes a plurality of optical fibers that extend generally parallel to the central axis of the nozzle.

6. A fuel injector as recited in claim 4, wherein the optical fibers are treated to withstand operating temperatures within the combustor.

7. A fuel injector as recited in claim 6, wherein the optical fibers are provided with a metal coating.

8. A fuel injector as recited in claim 4, wherein each optical fiber bundle is disposed within a temperature resistant guide tube.

9. A fuel injector as recited in claim 8, wherein each guide tube is formed from stainless steel.

10. A fuel injector as recited in claim 8, wherein each guide tube is cemented within a corresponding viewing port in a manner that accommodates thermal expansion and contraction.

11. A fuel injector as recited in claim 4, wherein each optical fiber bundle has a field of view of between about 14° and 30° relative to axis of fiber.

12. A fuel injector as recited in claim 8, wherein a lens is provided at the distal end of the guide tube for modifying the field of view of the optical fiber bundle disposed therein.

13. A fuel injector as recited in claim 8, wherein a window is provided at the distal end of the guide tube to seal the interior of the guide tube and protect the optical fiber bundle disposed therein.

14. A fuel injector as recited in claim 8, wherein distal end portions of the optical fibers of an optical fiber bundle are splayed radially outwardly to enhance the field of view of the optical fiber bundle.

15. A fuel injector as recited in claim 4, wherein the optical sensing means further includes at least one optical fiber mounted along the axis of the nozzle.

16. A fuel injector as recited in claim 1, wherein the optical sensing means communicates with means for processing optical signals.

17. A fuel injector as recited in claim 16, wherein the means for processing optical signals includes means for detecting combustion instabilities based upon conditions observed by the optical sensing means within the fuel nozzle.

18. A fuel injector as recited in claim 17, wherein the means for detecting combustion instabilities communicates with means for modulating the rate of fuel flow to the fuel injector to reduce detected combustion instabilities.

19. A fuel injector as recited in claim 4, wherein the optical fibers are UV enhanced fibers.

20. A fuel injector as recited in claim 4, wherein the optical fibers are IR enhanced fibers.

21. A fuel injector for a gas turbine combustor, comprising:
   a) a feed arm including means for attaching the fuel injector to the combustor; and
   b) a fuel nozzle having an upstream end associated with the feed arm and a downstream end for issuing fuel into the combustor, the fuel nozzle including a leading edge having a plurality of spaced apart viewing ports containing an optical sensor array for viewing conditions within the combustor downstream from said nozzle.

22. A fuel injector as recited in claim 21, wherein the fuel nozzle has a central axis and includes an outer swirler, wherein the outer swirler includes the leading edge of the fuel nozzle, and wherein the plurality of spaced apart viewing ports are located around the leading edge of the outer swirler.

23. A fuel injector as recited in claim 22, wherein the optical sensor array includes a plurality of optical fiber bundles, and wherein an optical fiber bundle is accommodated within each viewing port.

24. A fuel injector as recited in claim 23, wherein the optical fibers in each optical fiber bundle are treated to withstand operating temperatures within the combustor.

25. A fuel injector as recited in claim 23, wherein each optical fiber bundle is disposed within a temperature resistant guide tube.

26. A fuel injector as recited in claim 23, wherein the optical sensor array further includes at least one optical fiber are mounted along the axis of the nozzle.

27. A fuel injector as recited in claim 23, wherein the optical fibers are UV enhanced fibers.

28. A fuel injector as recited in claim 23, wherein the optical fibers are IR enhanced fibers.

29. A system for stabilizing combustion in a gas turbine engine, the system comprising:
   a) an optical sensing array embedded within a leadirnz edge of a fuel injector for observing conditions within a combustion chamber of a gas turbine engine;
   b) means for detecting combustion instabilities based upon conditions observed by the optical sensing array; and
   c) means for modulating a fuel flow rate to reduce detected combustion instabilities.

30. A system as recited in claim 29, wherein the means for detecting combustion instabilities includes means for detecting changes in flame intensity at levels indicative of flame instability.

31. A system as recited in claim 29, wherein the means for detecting combustion instabilities includes means for detecting spectral radiation indicative of fuel contaminants effecting fuel heat values.

32. A system as recited in claim 29, wherein the means for detecting combustion instabilities includes means for detecting spectral radiation indicative of chemical emissions effecting flame temperature, NOx, CO and fuel/air ratio.

33. A system as recited in claim 29, wherein the means for modulating fuel flow to reduce detected combustion instabilities includes a fuel control system operatively associated with a fuel pump.

* * * * *